United States Patent [19]

Buzza et al.

[11] 4,202,747
[45] May 13, 1980

[54] FLOW CELL FLUID AND SAMPLE SUPPLY MECHANISM

[75] Inventors: Edmund E. Buzza, Fullerton; Richard C. Meyer, La Habra, both of Calif.

[73] Assignee: Beckman Instruments, Inc., Fullerton, Calif.

[21] Appl. No.: 922,458

[22] Filed: Jul. 6, 1978

[51] Int. Cl.² .................................. G01N 27/46
[52] U.S. Cl. ........................... 204/195 R; 204/195 P; 204/195 G
[58] Field of Search ............ 204/1 T, 195 R; 422/50, 422/63, 98

[56] References Cited

U.S. PATENT DOCUMENTS

| | | | |
|---|---|---|---|
| 3,776,184 | 12/1973 | Harrison | 422/50 |
| 3,817,425 | 6/1974 | Liston | 222/1 |
| 3,853,008 | 12/1974 | Hoffa et al. | 422/63 |
| 3,997,420 | 12/1976 | Buzza | 204/195 G |
| 4,006,736 | 2/1977 | Kranys et al. | 128/2 A |
| 4,048,040 | 9/1977 | Schwartz | 204/195 R |

*Primary Examiner*—T. Tung
*Attorney, Agent, or Firm*—R. J. Steinmeyer; Robert R. Meads; John R. Shewmaker

[57] ABSTRACT

Apparatus for automatically and selectively supplying a blood sample or a wash/calibration solution to the entrance port of a flow cell which measures characteristics of the sample such as pH, $pCO_2$ and $pO_2$. A sample filled syringe and a solution supply conduit are supported by respective first and second fluid delivery mechanisms which rotate to move the syringe outlet and the conduit outlet in generally arcuate paths toward and away from the flow cell entrance port. The delivery mechanisms are rotated simultaneously, one toward and one away from the entrance port, by a common drive gear. Seating of the wash solution outlet in the entrance port is upstream of the seating of the sample outlet to ensure complete flushing of sample from the entrance port by the wash solution.

6 Claims, 3 Drawing Figures

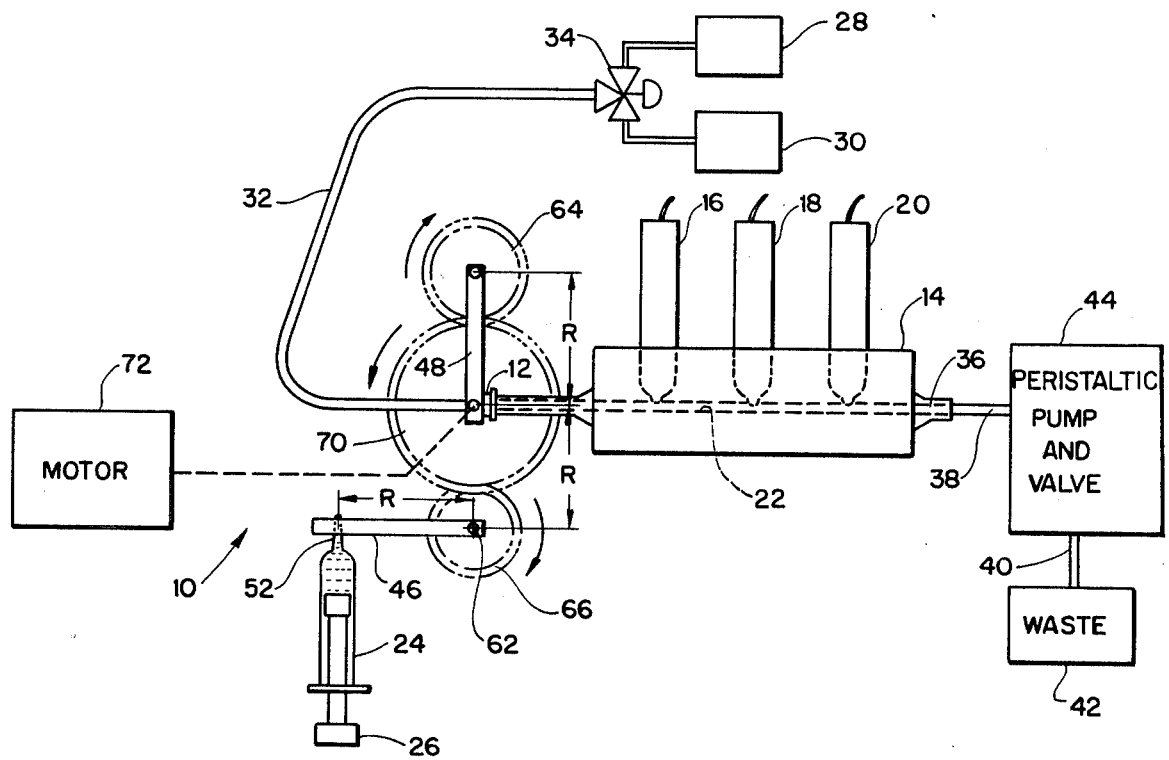
FIG. 1
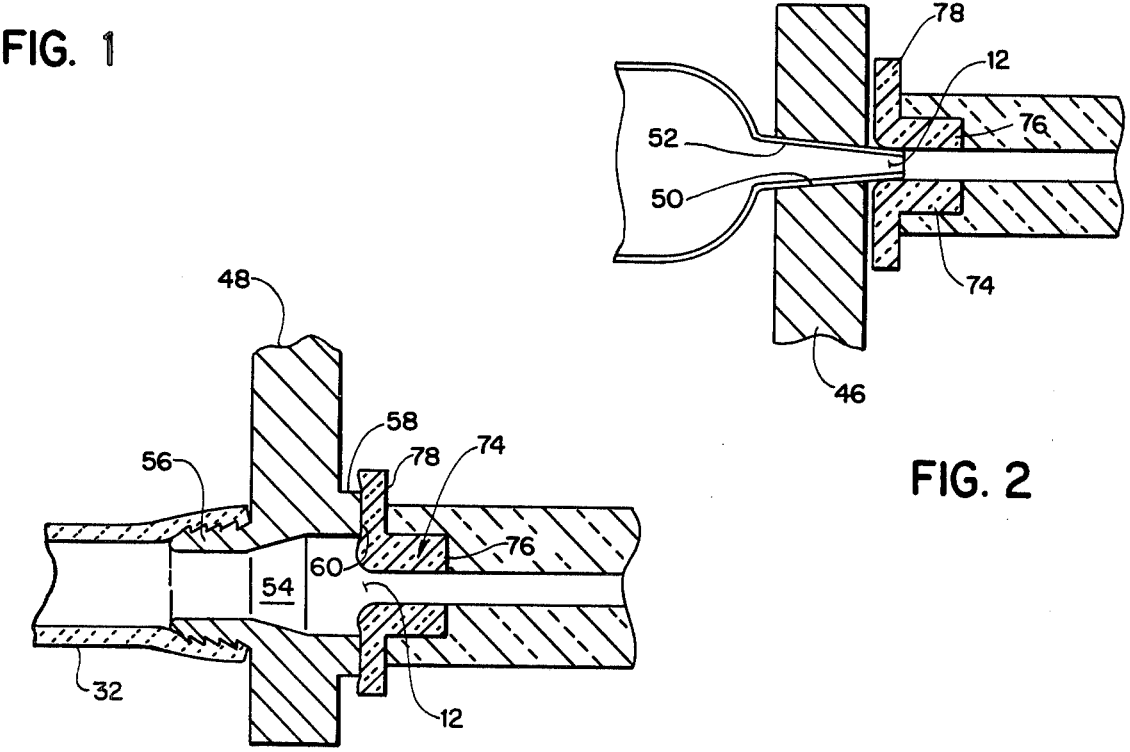
FIG. 2
FIG. 3

FLOW CELL FLUID AND SAMPLE SUPPLY MECHANISM

BACKGROUND OF THE INVENTION

1. Field of the Invention

The present invention relates generally to fluid flow cells and, more particularly, to mechanisms for supplying different fluids to such cells. The invention is particularly advantageous for supplying a sample, and a wash or calibration solution to the entrance port of flow cells adapted to analyze the sample material.

2. Description of the Prior Art

U.S. Pat. No. 3,997,420, assigned to the assignee of the present invention, describes a flow cell for use in blood chemistry analyses and in particular for determining the pH, $pCO_2$ and $pO_2$ of blood. The cell employs pH, $pCO_2$, and $pO_2$ measuring electrodes mounted adjacent a sample passage extending through the cell. A blood sample is collected in a conventional syringe and the syringe plunger is actuated to drive the sample through the flow cell passage in contact with each of the measuring electrodes. A wash solution is then conveyed through the passage to discharge the remaining sample therefrom to prepare the flow cell for receipt of the next injected sample. In addition, a calibration solution or gas is periodically conveyed through the passage, as required, to calibrate the measuring electrodes.

In the foregoing apparatus a sample filled syringe is secured by a leur fitting to a rotatable disc in alignment with a passage through the disc, and the disc is rotated to align the passage and hence the syringe outlet with the entrance port of the flow cell passage. The disc makes frictional sliding contact with the entrance port in a plane perpendicular thereto and hence is subject to sample leakage at the sliding contact. Moreover, the wash and calibration solutions, are introduced into the flow cell passage at a point downstream of the flow cell entrance port through a complicated arrangement of valves and pumps. Consequently, the flow of wash solution bypasses the entrance port thus requiring that an operator flush the port to prevent clogging and contamination of the port by a prior sample and resulting carryover of such contamination into subsequently injected samples.

SUMMARY OF THE INVENTION

The present invention resides in a novel fluid and sample supply mechanism which overcomes the operational drawbacks of the prior art. The supply mechanism is simple in construction and operation and enables repeatable delivery of sample and fluid without clogging or contamination and operator intervention attendant thereto.

To these ends, the present invention resides in a fluid and sample supply mechanism including sample supply means having an outlet for sample delivery, a first delivery mechanism supporting the sample supply means for presenting the outlet thereof to the fluid entrance port of the flow cell passage, and means for rotating the delivery mechanism about an axis generally perpendicular to the direction of flow through the fluid entrance port to move the supply outlet in an arcuate path toward and away from the fluid entrance port. The invention further includes fluid supply means having a fluid supply outlet, a second delivery mechanism supporting a fluid delivery means for presenting the outlet thereof to the entrance port, and means for rotating the second delivery mechanism about an axis perpendicular to flow through the entrance port to move the fluid delivery outlet in an arcuate path toward and away from the entrance port. Means is provided for controlling rotation of the first and second delivery mechanisms to selectively position the sample supply outlet or the fluid supply outlet at the flow cell entrance port for delivering sample or fluid, as required, through the entrance port into the flow cell passage. In the foregoing arrangement, both sample and fluid are selectively and automatically presented to the entrance port for delivery into the flow cell passage. The outlets approach and positively seat in the entrance port in the direction of fluid flow providing a fluid tight seal thereat and such seal is maintained by positive loading of the delivery mechanism.

The invention further contemplates drive means for simultaneously rotating the first and second delivery mechanisms one toward and away from the entrance port. In the preferred form, the delivery mechanisms are rotatable arms supporting, respectively, a sample filled syringe and a fluid supply conduit and adapted to be rotated by a common drive gear.

In position at the flow cell entrance port, the fluid supply outlet is aligned and seated at a location upstream of the corresponding location of the sample supply outlet. In this manner, fluid delivered through the fluid supply outlet flushes all sample remaining in the entrance port thereby precluding sample buildup and contamination of the entrance port and carryover contamination of subsequently introduced samples and eliminating operator intervention to clear the port.

BRIEF DESCRIPTION OF THE DRAWINGS

FIG. 1 is a diagram of a flow cell arrangement incorporating the improved sample and fluid supply mechanism of the invention.

FIG. 2 is an enlarged, fragmentary sectional view taken in a longitudinal direction through the flow cell entrance port and illustrates the alignment of a sample syringe at the entrance port for conveying sample through the port into the flow cell passage.

FIG. 3 is a view, similar to FIG. 2, illustrating alignment of a fluid supply conduit outlet at the flow cell entrance port for delivering fluid, such as wash and calibration solutions, through the port into the flow cell passage.

DESCRIPTION OF THE PREFERRED EMBODIMENT

As shown in the drawing for purposes of illustration, the present invention is embodied in a fluid and sample supply mechanism, indicated generally by numeral 10, for introducing fluids to the fluid entrance port 12 of a flow cell 14. The flow cell may be of the type disclosed in the aforementioned patent for analyzing blood samples delivered to the cell. To this end, the cell includes a plurality of electrochemical measuring electrodes 16, 18 and 20 having their lower sensing ends positioned to contact a sample flowing through a sample passage 22 extending through the flow cell. In the disclosed flow cell, the three measuring electrodes are sensitive, respectively, to sample pH, $pCO_2$, and $pO_2$. For further details regarding construction and operation of flow cell 14 per se, reference is made to the aforementioned patent which is specifically incorporated herein by reference.

It will be understood that operation of such a flow cell 14 requires means for delivering sample to the cell for measurement, for expelling sample from the cell following a measurement, and for flushing cell passage 22 periodically with a wash solution and/or a calibration soution or gas to prepare the measuring electrodes for the next sample measurement. To these ends, the sample is collected in a conventionalsyringe 24 having a plunger 26 for expelling fluid from the syringe. A wash solution reservoir 28 is provided containing the solution for flushing the sample passage 22 of the flow cell. The wash solution contains surface active agents and other agents or enzymes, as required, for conditioning and cleaning the sample passage. One or more reservoirs 30 of calibration solution or gas is provided for periodically supplying calibration fluid to calibrate the measuring electrodes. Calibration fluid comprises a predetermined and psychological normal concentration of the particular blood components or ions measured by the flow cell. A fluid supply conduit 32, selectively connected at one end to reservoirs 28 or 30 by a fluid switch 34 delivers the wash or calibration fluids to the flow cell 14.

The fluid exit port 36 of flow cell 14 is connected by conduit sections 38 and 40 to a waste receptacle 42 for conveying fluid exiting flowcell passage 22 to waste. Preferably, a combined peristaltic pump and valve 44 operatively coacts with conduit sections 38 and 40 to pump fluid through the flow cell toward waste or, alternatively, to allow fluid otherwise pumped through the cell to exit the cell toward waste. Reference is made to our copending application Ser. No. 922,457 for Combined Peristaltic Pump and Valve Controller, filed concurrently herewith, illustrating the describing the structure and operation of combined pump and valve 44.

The fluid and sample supply mechanism 10 of the invention includes a first delivery mechanism 46 supporting sample syringe 24 and a second delivery mechanism 48 supporting fluid supply conduit 32. Each delivery mechanism is illustrated as an elongate, structural arm or body. First delivery mechanism 46 includes a passage 50 therethrough into which the axially tapering tip 52 of syringe 24 is wedged securely to support the syringe on the delivery mechanism. As most clearly illustrated in FIG. 2, the tip 52 protrudes slightly beyond the end of passage 50. Second delivery mechanism 48 includes a passage 54 therethrough forming a coaxial extension the outlet of fluid supply conduit 32. As most clearly illustrated in FIG. 3, passage 54 is defined in part by a cylindrical lip 56 protruding from one side of delivery mechanism 48 and having a serrated outer circumferential surface around and over which the end of fluid supply conduit 32 is tightly wedged in fluid tight engagement. The outlet of passage 54 is defined by a cylindrical hub 58 on the opposite side of mechanism coaxial with passage 54 and which includes an annular end face 60 presented to the entrance port 12 in a plane perpendicular to the direction of flow into the entrance port.

Each of delivery mechanisms 46 ad 48 is supported at the end thereof opposite to respective passages 50 and54 therethrough for rotation in a manner to move the fluid outlet of sample syringe 24 and of fluid supply conduit 32 in an arcuate path toward and away from the entrance port 12 of flow cell 14. Mechanism 46 is supported at one end for rotation about an axis 62 while mechanism 48 is supported for rotation about axis 64. Each of axes 62 and 64 are offset from the axis of fluid flow through flow cell entrance port 12 by a radial distance R and extend in directions generally perpendicular to the direction of flow of fluid through the entrance port 12. In the drawing, rotational axes 62 and 64 extend perpendicularly relative to the plane of the drawing.

In the preferred embodiment, axes 62 and 64 are the axes of rotation of the shafts of respective driven gears 66 and 68. Delivery mechanisms 46 and 48 are rigidly affixed to the gear output shafts to be rotated in synchronism with gear rotation.

In accordance with a further aspect of the present invention, delivery mechanisms 46 and 48 are supported for simultaneous rotation in a manner moving the fluid outlets of sample supply syringe 24 and fluid supply conduit 32 in arcuate paths one toward and away from the flow cell entrance port 12. To this end, an intermediate drive gear 70 meshes with both driven gears 66 and 68 for simultaneously driving the same. In this regard the drive gear 70 is supported for turning on an axis intersecting and perpendicular to the axis of fluid flow through the cell entrance port 12 and parallel to the axes 62 and 64. Motive power for drive gear 70 is derived from a conventional bidirectional motor 72 adapted to drive the gear either clockwise or counterwise, as desired.

FIG. 1 illustrates the relative rotational positions of delivery mechanisms 46 and 48 in which the fluid outlet of supply conduit 32 is presented to and aligned with flow cell entrance port 12 while the fluid outlet of syringe 24 is removed therefrom. In order to remove the supply conduit outlet from the entrance port and present the syringe outlet thereto, drive gear 70 is driven in a counterclockwise direction thereby driving both of driven gears 66 and 68 in a clockwise direction. Clockwise rotation of second delivery mechanism 48 supporting fluid conduit 32 rotates delivery mechanism 48 about axis 64 in a clockwise direction to move the outlet of fluid conduit 32 in an arcuate path of radius R away from the entrance port. Simultaneously, first delivery mechanism 46 is rotated clockwise about axis 66 from the position illustrated in FIG. 1 moving the syringe outlet in an arcuate path of radius R until the syringe outlet is presented to and aligned with the entrance port. Bidirectional rotation of drive gear 70 by motor 72 thereby selectively positions the fluid outlet of one or the other of syringe 24 or fluid conduit 32 at the entrance port.

The entrance port 12 of the flow cell includes a resilient seating member 74 coaxial with flow cell passage 22 and having a first cylindrical section 76 extending axially along a portion of passage 22 and a second radially extending annular lip section 78 the leftward annular face in FIG. 2 of which defines a plane generally perpendicular to the direction of flow through the entrance port. As illustrated in FIG. 2, the axially tapering tip 52 of syringe 24 is adapted to engage and seat securely within the section 76 of seating member 74 forming an annular fluid tight seal therewith. With syringe 24 thus aligned and seated in the entrance port 12, syringe plunger 26 is depressed to inject sample through the entrance port into and through sample passage 22 past the measuring electrodes 16, 18 and 20. As noted in the aforementioned copending application, during such sample introduction, peristaltic pump and valve 44 is open to provide an open channel to allow fluid flow through and from the flow cell toward the waste receptacle 42.

In order to introduce wash or calibration fluids into the flow cell, second delivery mechanism 48 is rotated to the position of FIGS. 1 and 3. As most clearly illustrated in FIG. 3, annular face 60 of hub 58 engages the annular face of lip section 78 of seating member 74 to define an annular fluid tight seal therewith. Thus arranged, a flow path is provided from supply conduit 32 through outlet bore 54 of mechanism 48 and through entrance port 12. As taught in the aforementioned copending application, a flow of such solution may be affected by pumping action of pump 44.

In accordance with another aspect of the invention, the fluid supply outlet of supply conduit 32 is aligned with flow cell entrance port 12 in a manner ensuring complete flushing of prior sample or other contaminants from the delivery port. To this end the annular seal defined between hub 58 and seating member 74 is located upstream of the corresponding annular seal between syringe tip 52 and the seating member. In this manner, all surface area of the seating member on which sample could accumulate is subject to the flushing action of wash solution drawn through conduit 32 and passage 54.

An advantageous feature of the present mechanism results from the ability to stop rotation of drive gear 70 at a midpoint with both fluid supply outlets rotated away from the entrance port. At such time pump 44 can be actuated to pull air through the entrance port and flow cell passage 22 to expel prior fluid therefrom and flush such toward waste. In fact, such air flushing could be achieved without stopping gear 70 by actuating pump 44 while arms 46 and 48 are moving.

It will thus be seen that the flow cell fluid and sample supply mechanism 10 provides a simple and straightforward arrangement for automatically positioning and securely seating the sample supply outlet or a fluid supply outlet (e.g. wash or calibration) at the flow cell entrance port 12. The mechanism enables repeatable and accurate positioning of the two outlets in a fluid tight position in the entrance port and ensures a positive load while at the port and enables accurate delivery of fluid to and flushing of contaminants from the entrance port automatically without the need for operator intervention. While a preferred embodiment of the invention has been illustrated and described, it will be understood that modifications may be made therein without departing from the spirit and scope of the invention as defined by the appended claims.

What is claimed is:

1. In a flow cell for sample analysis including a passage therein for accommodating sample flow therethrough past sample measuring apparatus, the flow cell passage having a fluid entrance port, an improved fluid and sample supply mechanism comprising:
   sample supply means having an outlet through which sample is delivered;
   a first delivery mechanism supporting said sample supply means for presenting the outlet thereof to the fluid entrance port of said flow cell passage;
   means for rotating said first delivery mechanism about an axis of rotation generally perpendicular to the direction of flow through said fluid entrance port to move said outlet in an arcuate path toward and away from said fluid entrance port;
   fluid supply means including an outlet through which fluid is delivered;
   a second delivery mechanism supporting said fluid delivery means for presenting the outlet thereof to the fluid entrance port of said flow cell passage;
   means for rotating said second delivery mechanism about an axis of rotation generally perpendicular to the direction of flow through said fluid entrance port to move the fluid delivery outlet in an arcuate path toward and away from said fluid entrance port; and
   means for controlling the rotation of said first and second delivery mechanisms to selectively position the outlet of said sample supply means or the outlet of said fluid supply means at the fluid entrance port of the flow cell passage for delivering sample or fluid, as required, through said fluid entrance port into the flow cell passage.

2. The flow cell of claim 1 wherein the control means includes drive means for simultaneously rotating said first and second delivery mechanisms one toward and one away from the fluid entrance port of said flow cell passage.

3. The flow cell of claim 2 wherein said drive means includes first and second driven gears and means for connecting said first and second delivery mechanisms to the respective gears to be rotated thereby; and
   a common drive gear meshed with both said first and second driven gears for simultaneously driving the same.

4. The flow cell of claim 1 wherein said fluid entrance port includes a seating surface area against which the respective outlets of said sample supply means and said fluid supply means are engageable in a fluidtight seating relationship when positioned at said fluid entrance port, the respective outlets being dimensioned such that the fluid supply means outlet seats at a location upstream of the corresponding location of the sample supply means outlet to insure contact by said fluid of all areas of said entrance port contactable by said sample.

5. The flow cell of claim 4 wherein said seating surface of said fluid entrance port is defined by a resilient seating member having a first cylindrical section extending coaxially along a portion of the flow cell passage and a second radially extending section having an exposed face in a plane generally perpendicular to direction of flow through the fluid entrance port;
   said outlet of said sample supply means is defined by an axially tapering tip section which engages and seats within said first cylindrical section forming a first fluid tight seal therewith; and
   said outlet of said fluid supply means engages and seats against the exposed face of said second radially extending section forming a second fluid tight seal therewith upstream of said first fluid tight seal.

6. The flow cell of claim 1 further including:
   pumping means independent of the sample supply means and of the fluid supply means connected to the flow cell passage for pumping fluid therethrough; and
   means for enabling the pumping means with the first and second delivery mechanisms at respective rotational positions in which neither the sample supply means outlet nor the fluid supply means outlet is positioned at the fluid entrance port of the flow cell passage thereby enabling flushing of the flow cell passage with air pumped therethrough by the pumping means.

* * * * *